United States Patent [19]

Beier et al.

[11] Patent Number: 5,296,512
[45] Date of Patent: * Mar. 22, 1994

[54] WATER-SOLUBLE PRESSURE-SENSITIVE SKIN ADHESIVE, ITS USE, AND AGENTS PROVIDED WITH IT

[75] Inventors: Helmut Beier; Hans-Ulrich Petereit, both of Darmstadt; Gunter Bergmann, Hanau, all of Fed. Rep. of Germany

[73] Assignee: Rohm GmbH Chemische Fabrik, Darmstadt, Fed. Rep. of Germany

[*] Notice: The portion of the term of this patent subsequent to Jul. 28, 2009 has been disclaimed.

[21] Appl. No.: 896,790

[22] Filed: Jun. 9, 1992

Related U.S. Application Data

[63] Continuation of Ser. No. 514,971, Apr. 26, 1990, abandoned.

[30] Foreign Application Priority Data

Apr. 26, 1989 [DE] Fed. Rep. of Germany ....... 3913734

[51] Int. Cl.$^5$ ................. C08L 31/02; C08L 33/10
[52] U.S. Cl. ..................... 523/111; 524/560; 526/318.4; 424/443; 424/445; 424/447; 424/448; 424/485; 514/777; 514/944; 514/953; 602/54; 602/57
[58] Field of Search ............ 523/111; 524/560; 526/318.4; 424/448, 443, 445, 447, 485; 602/54, 57; 514/777, 944, 953

[56] References Cited

U.S. PATENT DOCUMENTS

| | | | |
|---|---|---|---|
| 3,740,366 | 6/1973 | Sanderson | 526/318.4 |
| 4,190,562 | 2/1980 | Westerman | 523/111 |
| 4,914,140 | 4/1990 | Saitoh | 523/111 |
| 5,009,224 | 4/1991 | Cole | 523/111 |
| 5,133,970 | 7/1992 | Petereit et al. | 424/443 |

OTHER PUBLICATIONS

Patent Abstracts of Japan, vol. II, No. 206 (C-433), Jul. 3, 1987.
WPI, File, Derwent An 73-65267U & JP-B 73-33973.
EP Report No. 90 10 7749.

*Primary Examiner*—Paul R. Michl
*Assistant Examiner*—John J. Guarriello
*Attorney, Agent, or Firm*—Oblon, Spivak, McClelland, Maier & Neustadt

[57] ABSTRACT

A salt of an uncrosslinked copolymer of a monoethylenically unsaturated mono- or dicarboxylic acid and an alkyl ester of acrylic or methacrylic acid is suitable as a pressure-sensitive skin adhesive for plasters, for transdermal pharmaceutical forms, or for fastening bandages, which is permanently flexible and can be washed off with water, for which the proportion of carboxylic acid has to be sufficient to make the copolymer water-soluble in the salt form.

18 Claims, No Drawings

WATER-SOLUBLE PRESSURE-SENSITIVE SKIN ADHESIVE, ITS USE, AND AGENTS PROVIDED WITH IT

This application is a continuation of application Ser. No. 07/514,971, filed on Apr. 26, 1990, now abandoned.

BACKGROUND OF THE INVENTION

1. Field of the Invention

This invention relates to a pressure-sensitive skin adhesive for fastening flat, flexible substrates such as adhesives, wound plasters, and adhesive plasters or transdermal drugs to the skin. A pressure-sensitive adhesive is one that is permanently flexible as a dried film and that removably fastens a solid substrate that is pressed on. However, the dried adhesive film does not have to be anhydrous. The desired adhesiveness frequently occurs only when the adhesive film is dried out in the air and does not dry further by itself, but is in moisture equilibrium with the skin.

This invention also relates to a solution of the pressure-sensitive skin adhesive and its use for application to flexible, flat substrates. Finally, the invention also relates to wound plasters and adhesive plasters and transdermal drugs.

2. Background of the Prior Art

A fastening agent for medical purposes consisting of an alcohol solution of polymers containing carboxyl groups, or interpolymers of polymerizable ethylene compounds and plasticizing or resinous substances, and optionally pigments and fillers is already known from DE-PS 855 615.

A suitable copolymer, for example, is made up of 40% methacrylic acid and 60% methyl methacrylate. Since by itself it is hard and not adhesive, 9 parts of polyvinyl methyl ether and 3 parts of glycerin are used as plasticizer with 2 parts of the copolymer. The mixture is applied to the skin from alcohol solution and is used to fasten bandages. The polymer film is water-resistant. However, since the copolymer is water-soluble in the form of its alkali metal salt, it can be washed off of the skin with a weakly alkaline soap solution.

EP-B 35 399 describes an adhesive polyacrylate for application to the skin that has a K value of 90 to 110 and is made up of 16-62% n-butyl acrylate, 34-80% 2-ethylhexyl acrylate, and 4-10% acrylic acid. Because of the high proportion of higher acrylic esters, the copolymer is soft and adhesive and does not require the addition of a plasticizer. This adhesive is processed from organic solution, for example in acetone, to make a pressure-sensitive adhesive film for a self-adhesive plaster or adhesive tape.

A pressure-sensitive skin adhesive whose adhesive strength on the skin depends strongly on the moisture content is disclosed by WO 84/03837. It contains a copolymer of a hydrophobic monomer from the group of alkyl esters of acrylic acid with 4 to 14 carbon atoms in the alkyl group, with 0.5-30% of a hydrophilic monomer from the group consisting of acrylic and/or methacrylic acid, acrylamide, and/or methacrylamide, itaconic acid, and vinylpyrrolidone, and 5-30% of another hydrophilic monomer such as polyethylene glycol acrylate or methacrylate.

Chem. Abstr. 99, 128 355 refers to JP-A 83/103 317, concerning an adhesive film for transdermal drugs that contains as the adhesive resin a copolymer of 0.1-15% of the ammonium salt of acrylic and/or methacrylic acid along with other monomers. The adhesive resin after adding water is applied to a carrier film in the form of a hydrosol. Ammonia escapes on drying, so that the acidic copolymer remains behind in the adhesive film.

Chem. Abstr. 98, 185 617 (JP-A 83/15 911) likewise describes an adhesive film for transdermal drugs. As adhesive resin it contains a crosslinked, partly neutralized polymer of an unsaturated carboxylic acid, with glycerin and gelatin as plasticizers. Because of the crosslinking the adhesive resin is insoluble.

In accordance with Chem. Abstr. 97, 188 313 (JP-A 82/134 415), copolymers of butyl acrylate and ammonium acrylate that are plasticized with polyoxypropylenesorbitan and crosslinked by polyepoxide resins are used for the same purpose.

SUMMARY OF THE INVENTION

The object of this invention is to provide a pressure-sensitive, permanently flexible pressure-sensitive skin adhesive that can be applied without using organic solvents and can be removed from the skin with water.

The pressure-sensitive skin adhesive pursuant to the invention contains a salt of an uncrosslinked copolymer of a monoethylenically unsaturated mono- or dicarboxylic acid that can be polymerized by a free radical mechanism, and at least one alkyl ester of acrylic and/or methacrylic acid. The copolymer is made up of such a proportion of the unsaturated carboxylic acid that it is soluble in water in the salt form.

The copolymer is considered to be water-soluble in the context of the invention when it provides a clear and homogeneous solution in pure water at 20° C. at a concentration of at least 1% in which the copolymer is present as a molecular dispersion.

The permanent flexibility properties, which are a prerequisite for pressure sensitivity, are achieved with a film containing moisture by a suitable choice of monomeric components of the underlying copolymer, or by the addition of organic plasticizers, or by a combination of these measures. Of course, the proportion of organic plasticizers should be as limited as possible or completely omitted, since the plasticizers frequently have the property of diffusing into the substrate or the skin. This property is not only physiologically undesirable, but also leads to the loss of adhesive strength when this depends essentially on the presence of the plasticizer. The preferred pressure-sensitive skin adhesives of the invention therefore contain a maximum of 20 wt. %, and with particular preference, no organic plasticizer at all.

Water has a distinct plasticizing action on the copolymers used pursuant to the invention, which usually becomes effective when applied to the skin, since the pressure-sensitive skin adhesive film is in moisture equilibrium with the skin. When preparing pressure-sensitive skin adhesive films on substrates, it is not desirable for the same reason to dry the film beyond this equilibrium value. The desired adhesiveness usually occurs with a moisture content of 1 to 10 wt. % based on the anhydrous copolymer.

The pressure-sensitive skin adhesive is considered to have pressure-sensitive adhesion in the context of the invention when it has an adhesive force of at least 1N/cm in the adhesive test according to European Pharmacopoeia, Second Edition, Part II-7, pp. 273 ff (1984) (peel method).

DETAILED DESCRIPTION OF THE INVENTION

It is known that the higher alkyl esters of acrylic and/or methacrylic acid impart softness and adhesiveness to the copolymers prepared from them. At the same time, they make the copolymer hydrophobic and water-insoluble. In determining the proportion of monoethylenically unsaturated carboxylic acid that can be polymerized by a free radical mechanism, care must therefore be taken that it is large enough on the one hand to provide solubility in water, and small enough on the other hand to leave room for an adequate proportion of the plasticizing alkyl acrylate or methacrylate. When the monomers used to prepare the copolymer do not permit both of these properties to be achieved at the same time, a plasticizer may be used for assistance.

The monoethylenically unsaturated mono- or dicarboxylic acid that can be polymerized by a free radical mechanism preferably has the structure $$R-CH=CR'-COOH$$

in which either

R stands for a hydrogen atom and R' stands for a hydrogen atom, a methyl group, or a $-CH_2-COOH$ group, or R stands for a $-COOH$ group and R' stands for a hydrogen atom.

Among these carboxylic acids are acrylic and methacrylic acid, itaconic acid, maleic acid, and fumaric acid. The proportion of monoethylenically unsaturated mono- or dicarboxylic acid is preferably from 30 to 80 wt. %, particularly 50 to 70 wt. % of the copolymer.

It is basically not necessary for all of the carboxylic acid units of the copolymer to be present in the salt form, but a fraction that provides water solubility is sufficient. The fraction necessary for this depends on the size and hydrophobicity of the ester fraction. In many cases a content of only 15 wt. % of carboxylate units is sufficient to make the copolymer water-soluble. The content of carboxylate monomer units is generally 20 to 50 wt. %.

Water solubility of the polymer can be achieved by partial neutralization of the carboxyl groups present, which is between 20 and 50 mole-% depending on the content of carboxylic acid monomer units. For practical application, degrees of neutralization of 50 to 100, particularly 70 to 100 mole-% are preferred. The viscosity of the adhesive solution and the adhesive force of the pressure-sensitive adhesive film can be controlled by means of the degree of neutralization.

Salt-forming cations that may be mentioned primarily are alkali metal cations, especially sodium and potassium. Other metal cations can be used only if they do not cause crosslinking by polyvalence and do not have an unwanted physiological action. Organic ammonium cations are suitable if they do not escape on drying or during storage in the form of the corresponding amine vapor. Also useful, for example, are quaternary ammonium cations that are derived from relatively nonvolatile, physiologically harmless amines such as diethanolamine or triethanolamine.

Preferred alkyl esters of acrylic acid and/or methacrylic acid are those with 1 to 12 carbon atoms in the alkyl group, especially the esters of acrylic acid. In particular, methyl, ethyl, n-butyl, n-hexyl, n-octyl, 2-ethylhexyl, n-decyl, and n-dodecyl acrylate are very suitable. The low esters of acrylic and/or methacrylic acid are generally used only as comonomers along with the higher esters. In addition, other comonomers can participate in the makeup of the copolymer if they do not unallowably reduce the water solubility or unallowably increase the hardness. Examples are acrylamide and/or methacrylamide, hydroxyalkyl esters and polyalkylene glycol esters of acrylic and/or methacrylic acid, ethylene, vinyl acetate, vinyl propionate, and vinylpyrrolidone. It is not usually necessary to use these monomers also to prepare useful pressure-sensitive skin adhesives; their fraction is ordinarily below 20 wt. %.

The copolymer can be produced in the salt form by free radical copolymerization of the neutralized carboxylic acid with the other monomeric constituents in aqueous solution. However, it is preferred first to make the unneutralized copolymer by using the free mono- or dicarboxylic acid. Various long-known polymerization procedures are available for the free radical polymerization of these monomer mixtures, for example polymerization in water or in organic solvents, polymerization in bulk, and since the copolymers are sparingly water-soluble in the acid form, emulsion polymerization in the aqueous phase is also suitable. The organic polymer solutions and aqueous polymer dispersions can be converted into powdered products by spray drying, for example. The bulk polymers are melted in an extruder and extruded to a fine granulate.

The molecular weight of the copolymer affects the viscosity of the aqueous solution of the pressure-sensitive skin adhesive depending on the concentration, based on the liquid constituent. It is preferably in the range between 20,000 and 2.5 million. The viscosity of the aqueous solution of the copolymer should be no more than 100 Pa.s, preferably 10 mPa.s to 10 Pa.s, with the polymer content of the solution preferably being about 20 to 70 wt. %.

The aqueous solution can be made by stirring the finely divided copolymer in the acid form in an aqueous solution of a base, with the copolymer dissolving with the formation of a salt. Plasticizers and other additives can optionally be added to the finished solution. Suitable plasticizers are liquid organic substances with at least limited water solubility that are compatible with the polymer and are nonvolatile or not significantly volatile under the conditions of processing and use. They should also be nontoxic and preferably should not migrate into the skin or the cemented substrate. There is adequate compatibility when a homogeneous solution can be prepared from the copolymer and the plasticizer, and a clear film can be prepared from this by drying, or when the copolymer can be dissolved in an excess of the plasticizer. Substances suitable as plasticizers usually have a molecular weight between 200 and 20,000 and contain one or more hydrophilic groups in the molecule, for example hydroxy, ether, or amino groups.

Examples of suitable plasticizers are triethyl citrate or tributyl citrate, glycerin triacetate, and Polyethylene Glycols 200 to 20,000.

Use of the Aqueous Pressure-Sensitive Skin Adhesive Solution

Because of its nontoxic and nonirritating properties, the aqueous pressure-sensitive skin adhesive solution can be applied directly to the skin to form an adhesive surface. After brief drying, the adhesive film can be used to fasten bandages, support stockings, bodices, etc., by pressing them gently onto the film. The cemented substrate can be taken off easily after completion of the intended time of action, which can optionally be facilitated by moistening with water. No irritation is observed even when the same areas of skin are coated repeatedly. Because of the hydrophilic nature of the adhesive film, the skin is clearly less involved than when conventional rubber adhesive films are used. The adhesive film remaining on the skin including adhering dirt, fabric fibers, etc., can be washed off easily and quickly with hot or cold water.

The aqueous pressure-sensitive skin adhesive solution is suitable in the same way for producing pressure-sensitive adhesive films with skin adhesion for wound plasters, medical adhesive plasters, and adhesive tapes, or of drugs with transdermal action intended for application to the skin. They can contain a topical or systemic pharmaceutical ingredient, which may be contained in the adhesive film itself or in the coated substrate. The dried adhesive film, which still contains a sufficient amount of moisture, is preferably protected with a release film until it is used.

To produce the adhesive film, a film of the aqueous pressure-sensitive adhesive solution 0.01 to 1 mm thick is applied to the substrate, and dried for 1 min to 24 hours at 20° to 100° C., for example, during which the moisture content should not be allowed to drop below that necessary to maintain the desired adhesiveness. If desired, the coating can be repeated several times to reach a greater thickness. Flexible, flat substrates are suitable for coating, for example the familiar fabrics, nonwoven fabrics, or films of plastic or metal, especially aluminum, that are customary for adhesive plasters. Special polymer films that serve as drug reservoirs, for example, and their laminates with metal foils can also be provided with an adhesive film. It is felt to be advantageous in the industrial application of the pressure-sensitive skin adhesive pursuant to the invention that no environmentally polluting or explosive solvent vapors from the drying zone require disposal, and that the coating system can be cleaned with just water.

EXAMPLES

Example 1

12.5 g of sodium hydroxide is dissolved in 265.5 q of purified water. To this solution is added 70.5 g of an anionic copolymer of ethyl acrylate and methacrylic acid (1:1 ratio by weight, commercial product ®EUDRAGIT L 100-155, Röhm GmbH), and it is dissolved with constant stirring. 106.0 g of polyethylene glycol (mol. wt. 400) and 45.6 g of anhydrous glycerin are then mixed in. The solution with a solids content of 46.9 wt. % has a viscosity of 1925 mPas (Brookfield, II/6/20). It is coated on an aluminum foil with a wet film thickness of 500 μm using a doctor bar, and dried at 80° C. The amount of adhesive applied is about 13 mg/cm$^2$. The adhesive film achieves an adhesive force of 5.4N/cm.

Example 2

282 g of an anionic copolymer of methyl methacrylate and methacrylic acid (1:1 ratio by weight, commercial product ®EUDRAGIT L 100, Röhm GmbH) is suspended in 762 g of purified water and preswollen with stirring for 10 min. A solution of 50 g of sodium hydroxide in 300 g of purified water is mixed with this batch and is stirred until the solution of polymer is clear. 424 g of polyethylene glycol (mol. wt. 400) and 182 g of anhydrous glycerin are then mixed in. The solution has a solids content of 46.9% and a viscosity of 1650 mPas (Brookfield, II/6/20). 60 ml of this formulation is loaded into a roll-on applicator. When the solution is coated on the skin, an adhesive film is formed after drying that securely fastens support hose. No skin irritation is found even after several days. Residues of adhesive on the skin and the hose fabric can be washed off easily with water.

Example 3

50 g of an anionic copolymer of methyl methacrylate and methacrylic acid (1:2 ratio by weight, commercial product ®EUDISPERT hv, Röhm GmbH) is suspended in 450 g of purified water and preswollen by stirring for 10 min. A solution of 12 g of sodium hydroxide in 238 g of purified water is mixed with this batch and stirred in, until the solution of the polymer is clear. 50 g of triethyl citrate and 200 g of anhydrous glycerin are then added. This gel dries on the skin to an adhesive film that holds fabric or bandages against slipping.

Example 4

65.6 g of an anionic copolymer of methyl methacrylate and methacrylic acid (1:1 ratio by weight, commercial product ®EUDRAGIT L 100, Röhm GmbH) is heated in 239.2 g of purified water with stirring at 80° to 90° C., and 54.3 g of triethanolamine is added. The batch is cooled with continued stirring to 30° to 35° C., and 98.4 g of polyethylene glycol (mol. wt. 400) and 42.5 g of anhydrous glycerin are mixed in. The solution has a solids content of 52.2 wt. % and a viscosity of 1350 mPas (Brookfield, II/6/20). It is applied to an aluminum foil with a wet film thickness of 500 μm with a doctor bar and dried at 80° C. The adhesive film achieves an adhesive force of 2.5N/cm with an amount applied of 13 mg/cm$^2$.

Example 5

67.5 g of an anionic copolymer of ethyl acrylate and methacrylic acid (1:1 ratio by weight, commercial product ®EUDRAGIT L 100-55, Röhm GmbH) is suspended in 100 g of purified water and preswollen with stirring for 10 min. A solution of 12 g of sodium hydroxide and 60 g of purified water is mixed with this batch, and the mixture is stirred until the solution of the polymer is clear. 101.5 g of polyethylene glycol (mol. wt. 400) and a solution consisting of 67.5 g of urea and 91.5 g of purified water are then mixed in. The solution is applied to a soft PVC film (Guttagena-Folie WK 68 SLIM, Kalle Co., D-6200 Wiesbaden) by means of a doctor bar with a wet film thickness of 500 μm, and is dried at 80° C. The film adheres to human skin for several hours. The adhesive film with an amount applied of 13 mg/cm$^2$ achieves an adhesive force of 5.0N/cm.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A method of applying a permanently flexible pressure-sensitive skin adhesive coating to a substrate from which it is removable by washing with water, which consists essentially of the steps of coating said substrate with a layer of an aqueous solution consisting essentially of water and a salt of an uncrosslinked copolymer of:

(a) a monoethylenically unsaturated mono- or dicarboxylic acid that can be polymerized by a free radical mechanism and (b) at least one alkyl ester of (meth)acrylic acid, wherein the copolymer contains such a portion of said unsaturated mono- or dicarboxylic acid that it is water soluble in the salt form, and drying said coated layer to form a pressure-sensitive coating.

2. A method of applying a permanently flexible pressure-sensitive skin adhesive coating to a substrate from which it is removable by washing with water, which consists essentially of the steps of coating said substrate with a layer of an aqueous solution consisting essentially of water, at least one organic plasticizer and a salt of an uncrosslinked copolymer of (a) a monoethylenically unsaturated mono- or dicarboxylic acid that can be polymerized by a free radical mechanism and (b) at least one alkyl ester of (meth)acrylic acid wherein the copolymer contains such a portion of said unsaturated mono- or dicarboxylic acid that it is water soluble in the salt form, and drying said coating layer to form a pressure-sensitive coating.

3. A method of applying a pressure-sensitive skin adhesive coating according to claim 1, wherein the copolymer contains such a proportion of the unsaturated carboxylic acid that it is soluble in water with 20 to 50% neutralization of the carboxylic acid units.

4. A method of applying a pressure-sensitive skin adhesive coating according to claim 1, wherein the monoethylenically unsaturated mono- or dicarboxylic acid that can be polymerized by a free radical mechanism has the structure $$R-CH=CR'-COOH$$

in which either
(X) R stands for a hydrogen atom and R' stands for a hydrogen atom, a methyl group, or a $-CH_2-COOH$, or
(Y) R stands for a $-COOH$ group and R' stands for a hydrogen atoms.

5. A method of applying a pressure-sensitive skin adhesive coating according to claim 1, wherein the copolymer contains 30 to 80 wt. % of the ethylenically unsaturated carboxylic acid that can be polymerized by a free radical mechanism.

6. A method of applying a pressure-sensitive skin adhesive coating according to claim 1, wherein the copolymer contains an alkyl ester of acrylic and/or methacrylic acid with 1 to 14 carbon atoms in the alkyl group.

7. A method of applying a pressure-sensitive skin adhesive coating according to claim 1, wherein the carboxyl groups of the copolymer are neutralized to the extent of 50 to 100 mol-%.

8. The method of applying a pressure-sensitive skin adhesive coating according to claim 1, wherein said aqueous solution contains 20 to 90 wt. % water.

9. A method of applying a pressure-sensitive skin adhesive coating according to claim 1, wherein said substrate is a wound plaster component.

10. A method of applying a pressure-sensitive skin adhesive coating according to claim 2, wherein the copolymer contains such a proportion of the unsaturated carboxylic acid that it is soluble in water with 20 to 50% neutralization of the carboxylic acid units.

11. A method of applying a pressure-sensitive skin adhesive coating according to claim 2, wherein the monoethylenically unsaturated mono- or dicarboxylic acid that can be polymerized by a free radical mechanism has the structure $$R-CH=CR'-COOH$$

in which either
(X) R stands for a hydrogen atom and R' stands for a hydrogen atom, a methyl group, or a $-CH_2-COOH$, or
(Y) R stands for a $-COOH$ group and R' stands for a hydrogen atom.

12. A method of applying a pressure-sensitive skin adhesive coating according to claim 2, wherein the copolymer contains 30 to 80 wt. % of the ethylenically unsaturated carboxylic acid that can be polymerized by a free radical mechanism.

13. A method of applying a pressure-sensitive skin adhesive coating according to claim 2, wherein the copolymer contains an alkyl ester of acrylic and/or methacrylic acid with 1 to 14 carbon atoms in the alkyl group.

14. A method of applying a pressure-sensitive skin adhesive coating according to claim 2, wherein the carboxyl groups of the copolymer are neutralized to the extent of 50 to 100 mol-%.

15. A method of applying a pressure-sensitive skin adhesive coating according to claim 2, wherein the aqueous solution contains 2 to 200 wt. % of a plasticizer for the salt of the copolymer.

16. A method of applying a pressure-sensitive skin adhesive coating according to claim 2, wherein said aqueous solution contains 20 to 90 wt. % water.

17. A method of applying a pressure-sensitive skin adhesive coating according to claim 2, wherein said substrate is a wound plaster component.

18. A method of applying a permanently flexible pressure sensitive skin adhesive coating to a substrate from which it is removable by washing with water, which consists essentially of the steps of coating said substrate with a layer of an aqueous solution consisting essentially of water, a topical or systemic pharmaceutical ingredient and a salt of an uncrosslinked copolymer of:

(a) a monoethylenically unsaturated mono- or dicarboxylic acid that can be polymerized by a free radical mechanism and (b) at least one alkyl ester of (meth)acrylic acid, wherein the copolymer contains such a portion of said unsaturated mono- or dicarboxylic acid that it is water soluble in the salt form, and drying said coated layer to form a pressure-sensitive coating.

* * * * *